(12) United States Patent
Kabaha et al.

(10) Patent No.: US 10,053,663 B2
(45) Date of Patent: Aug. 21, 2018

(54) CENTRIFUGATION CHAMBER WITH GAS PERMEABLE MEMBRANE LAYERS FOR CELL CULTIVATION

(71) Applicant: Miltenyi Biotec GmbH, Bergisch Gladbach (DE)

(72) Inventors: Eiad Kabaha, Bonn (DE); Stefan Miltenyi, Bergische Gladbach (DE); Ralf-Peter Peters, Bergisch Gladbach (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 170 days.

(21) Appl. No.: 15/161,317

(22) Filed: May 23, 2016

(65) Prior Publication Data

US 2016/0264919 A1   Sep. 15, 2016

Related U.S. Application Data

(63) Continuation-in-part of application No. 14/312,573, filed on Jun. 23, 2014, now abandoned.

(30) Foreign Application Priority Data

Jul. 2, 2013   (DE) .................................... 13174602
Jul. 2, 2013   (DE) .................................... 13174604

(51) Int. Cl.
| | |
|---|---|
| *C12M 3/00* | (2006.01) |
| *C12M 1/00* | (2006.01) |
| *C12M 1/26* | (2006.01) |
| *C12M 1/12* | (2006.01) |
| *B04B 5/10* | (2006.01) |

(Continued)

(52) U.S. Cl.
CPC ............... *C12M 33/10* (2013.01); *B04B 1/00* (2013.01); *B04B 5/0442* (2013.01); *B04B 5/10* (2013.01); *B04B 7/12* (2013.01); *B04B 11/06* (2013.01); *C12M 23/24* (2013.01); *C12M 25/02* (2013.01);

(Continued)

(58) Field of Classification Search
CPC ...... C12M 23/24; C12M 25/06; C12M 27/10; C12M 47/04
See application file for complete search history.

(56) References Cited

U.S. PATENT DOCUMENTS

| | | |
|---|---|---|
| 5,837,150 A | 11/1998 | Langley et al. |
| 5,879,280 A | 3/1999 | Hlavinka et al. |

(Continued)

FOREIGN PATENT DOCUMENTS

| | | |
|---|---|---|
| EP | 2594632 | 5/2013 |
| JP | H06225758 | 8/1994 |
| WO | WO 2009/072006 | 6/2009 |

OTHER PUBLICATIONS

U.S. Appl. No. 14/312,573, filed Jun. 23, 2014, Kabaha, et al.

*Primary Examiner* — Nathan A Bowers
(74) *Attorney, Agent, or Firm* — Jaquelin K. Spong

(57) ABSTRACT

The invention is directed to a centrifuge chamber comprising a cylinder having a base plate and a cover plate, a rotational axis with at least one port for input and/or output of liquids, at least one port for input of gases and at least one layer for cell culturing, wherein the layer for cell culturing comprises a gas-permeable membrane on which cells can be cultured and wherein the at least one port for input and/or output of gases is connected to the gas-permeable membrane.

15 Claims, 14 Drawing Sheets

(51) Int. Cl.
*B04B 1/00* (2006.01)
*B04B 5/04* (2006.01)
*B04B 7/12* (2006.01)
*B04B 11/06* (2006.01)
*C12M 1/04* (2006.01)

(52) U.S. Cl.
CPC ............ *C12M 29/04* (2013.01); *C12M 29/06* (2013.01); *C12M 47/02* (2013.01)

(56) References Cited

U.S. PATENT DOCUMENTS

| | | |
|---|---|---|
| 6,001,642 A | 12/1999 | Tsao |
| 2007/0026516 A1* | 2/2007 | Martin .................. C12M 23/04 435/297.5 |
| 2009/0298163 A1* | 12/2009 | Bennett ................ C12M 23/08 435/294.1 |
| 2010/0311559 A1* | 12/2010 | Miltenyi ............ A61M 1/3693 494/10 |
| 2011/0226686 A1* | 9/2011 | Maurer ............... A61M 1/1698 210/206 |

\* cited by examiner

CENTRIFUGATION CHAMBER WITH GAS PERMEABLE MEMBRANE LAYERS FOR CELL CULTIVATION

CROSS REFERENCE TO RELATED APPLICATIONS

This application is a continuation-in-part of U.S. patent application Ser. No. 14/312,573, filed Jun. 23, 2014, which claims priority to European Application No. EP13174604.2, and European Application No. EP13174602.6, both filed Jul. 2, 2013, the contents of which are incorporated herein by reference in their entirety.

STATEMENT REGARDING FEDERALLY SPONSORED RESEARCH

Not applicable.

STATEMENT REGARDING MICROFICHE APPENDIX

Not applicable.

BACKGROUND

The invention relates to a centrifuge chamber for biological samples.

Fractionation and separation of cells from suspensions like blood or bone marrow is becoming more and more part of medical treatment. For such treatment, cells are extracted from a patient then separated to provide the desired target cells which are usually stimulated/manipulated/expanded by cell culturing before introducing into the same or a different patient. Extracting, preparation, fractionation, separation, manipulation and introducing of the cells should be performed as fast as possible to reduce stress imposed on the target cells and the patients. Contrary to these requirements, cell culturing is a laborious and time-consuming process.

Fractionation and separation of cell suspensions by centrifugation are long known in the art to separate samples of biological origin into two or more components. For example, the separation of human blood into leucocytes, erythrocytes and blood plasma is an often performed process and can be conduced in a semi automated apparatuses as disclosed in U.S. Pat. No. 6,605,223, U.S. Pat. No. 4,446,014 or U.S. Pat. No. 81,242,342. These publications are silent about cell culturing.

WO 2009/072006 and WO 2009/072003 disclose a centrifugation system with centrifugation chambers suitable for cell separation. The chamber can be provided with layers for adhering and culturing the separated cells. WO 2009/072006 and WO 2009/072003 are silent about the cell culturing conditions and the supply of the cells with gases and nutrition. This centrifugation system and/or centrifugation chambers are optimized for cell separation rather than cell culturing of the separated cells.

SUMMARY

Since new cell therapies require not only separation of target cells, but also expansion of the target cells to provide a sufficient number of cells, it is an object of the invention to provide a centrifugation chamber which allows cell separation and cell culture in the same centrifugation chamber and in an automated process. A crucial point in cell culture is the supply of the cells with gases such as oxygen or carbon dioxide.

Accordingly, an object of the present invention is to provide a centrifuge chamber enabling cell cultivation and cell separation in a single container without manual manipulation of the cells.

Accordingly it is an object of the invention to provide a centrifuge chamber having a rotational axis and an outer wall substantially parallel to the rotational axis, and comprising a base plate and a cover plate, at least one port for liquids, at least one port for gases and a at least one layer for cell culturing, wherein each layer for cell culturing comprises a gas-permeable membrane on which cells are cultured, and wherein the base plate is coupled to a gas port and to the gas permeable membrane, so that the gas port is in gaseous communication with the gas permeable membrane.

A plurality of such layers may be assembled into a stack, wherein each layer includes a gas-permeable membrane on which cells are cultured. Each layer may be coupled to an adjacent layer. The first layer may be coupled to at least one gas port. The membranes may be disposed on a support structure whereupon each layer is connected to the adjacent layers or the ports for input and/or output of gases by at least one opening.

Cell culturing on the gas-permeable membrane, according to the invention, relates to all methods where cells are kept physiologically active and optionally are modified. The modification may result, for example, in a change of the phenotype, function, number or differentiation status of the cells. Cell culturing on the gas-permeable membrane according to the invention may lead to a) cell division, differentiation or cell proliferation
b) activation of a signal transduction cascade
c) change of the cellular activation status and/or cell function
d) genetic modification of cells
e) growing of layers of different or identical cell types involving cell-cell contact In the centrifuge chamber according to the invention, the gas-permeable membranes can be applied on a support structure. Accordingly, the gas-permeable membrane has a first surface on which the cells are cultured ("cell-side") and a second surface, to which the gases are supplied ("gas-side"). To supply the cells, gas migrates from the gas-side of the membrane to the cell-side.

The first gas-permeable membrane (first in the direction of gas-flow) may be applied on the base plate of the chamber or on a first support structure. At least one port for input of gases to the chamber is connected to the first gas-permeable membrane, which means that gases can be supplied to the volume between the first gas-permeable membrane and the base plate or to the volume between the gas-permeable membrane and the first support structure.

BRIEF DESCRIPTION OF THE DRAWINGS

Various exemplary details are described with reference to the following figures, wherein.

DETAILED DESCRIPTION

Figure 1:
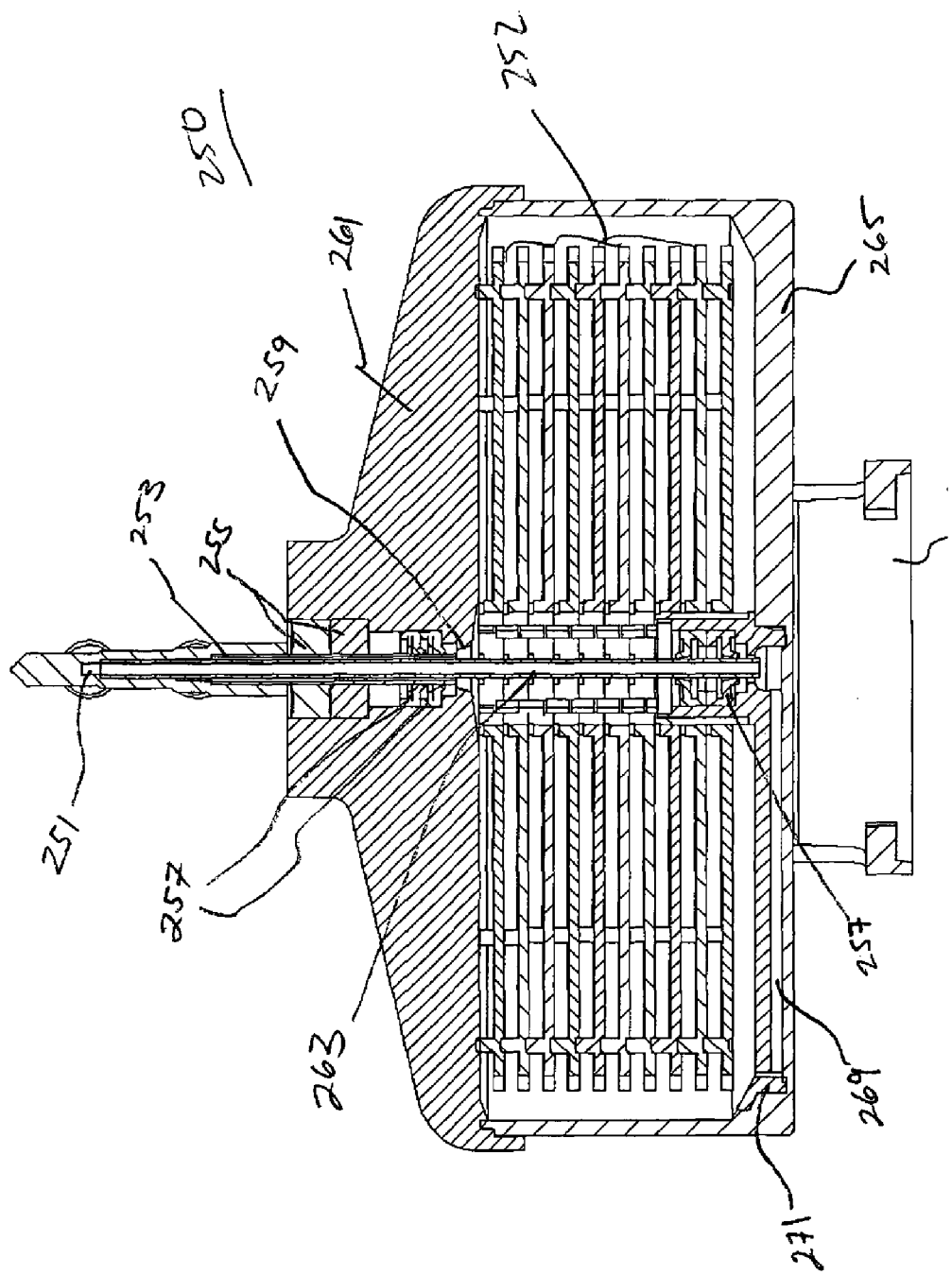
FIG. 1 shows a cross sectional view of a standard centrifuge chamber according to the prior art.

FIG. 1 shows a standard centrifuge chamber according to the prior art, for example as disclosed in WO 2009/072006 or WO 2009/072003. This centrifuge chamber is provided with two input/output ports in the axis of the chamber connected via tubes to openings into the chamber and layers for cell culture. The cells are supplied with gas and cell culture media via the input/output ports and by diffusion through the liquid in the whole chamber. The supply of the cells with gases in such a system will be insufficient and/or inhomogeneous since cells at the periphery of the layers or adjacent to the input/output ports will be better supplied than cells adhered more towards the rotational axis.

General Description of the Centrifugation Chamber of the Invention

The chamber according to the invention may comprise a circular base plate and a circular cover plate, both of which may be oriented substantially perpendicular to a rotational axis; and a cylinder or a outer wall which may be oriented substantially perpendicular to the base and cover plate and parallel to the rotational axis. In this configuration, the base plate, cover plate and cylinder or outer wall can be glued or welded together in a water and gas-tight fashion. Thereby, a closed centrifugation chamber may be formed, comprising base plate (15) and an upper cover plate (18) in the form of a lid. A cylinder or outer wall (16) may be sealed between the baseplate (15) and the cover plate (18) to form a substantially circular outer wall which is substantially parallel to the rotational axis, as shown in FIG. 2.

Accordingly, the centrifuge chamber may have a rotational axis and an outer wall substantially parallel to the rotational axis, and may comprise a base plate and a cover plate, at least one port for liquids, at least one port for gases and a at least one layer for cell culturing, wherein each layer for cell culturing comprises a gas-permeable membrane on which cells are cultured, and wherein the base plate is coupled to a gas port and to at least one gas permeable membrane, so that the gas port is in gaseous communication with the at least one gas permeable membrane. The gas permeable membrane may be coupled to at least one of the support structure and the base plate in a gas tight manner. In one embodiment, the cell layer for culturing may have a gas-permeable membrane on which cells are cultured, and a rigid support that supports the gas-permeable membrane, and wherein the both the gas-permeable membrane and the rigid support each have a through hole structure formed therein, wherein the through hole structure in the membrane fits over the through hole structure in the rigid support, thereby defining their relative orientation, and wherein the membrane further has spacers that allow the flow of gas from the through hole structures to a volume between the membrane and the rigid support, and wherein the base plate is coupled to a gas port and to at least one gas permeable membrane, so that the gas port is in gaseous communication with the at least one gas permeable membrane.

Figure 2:
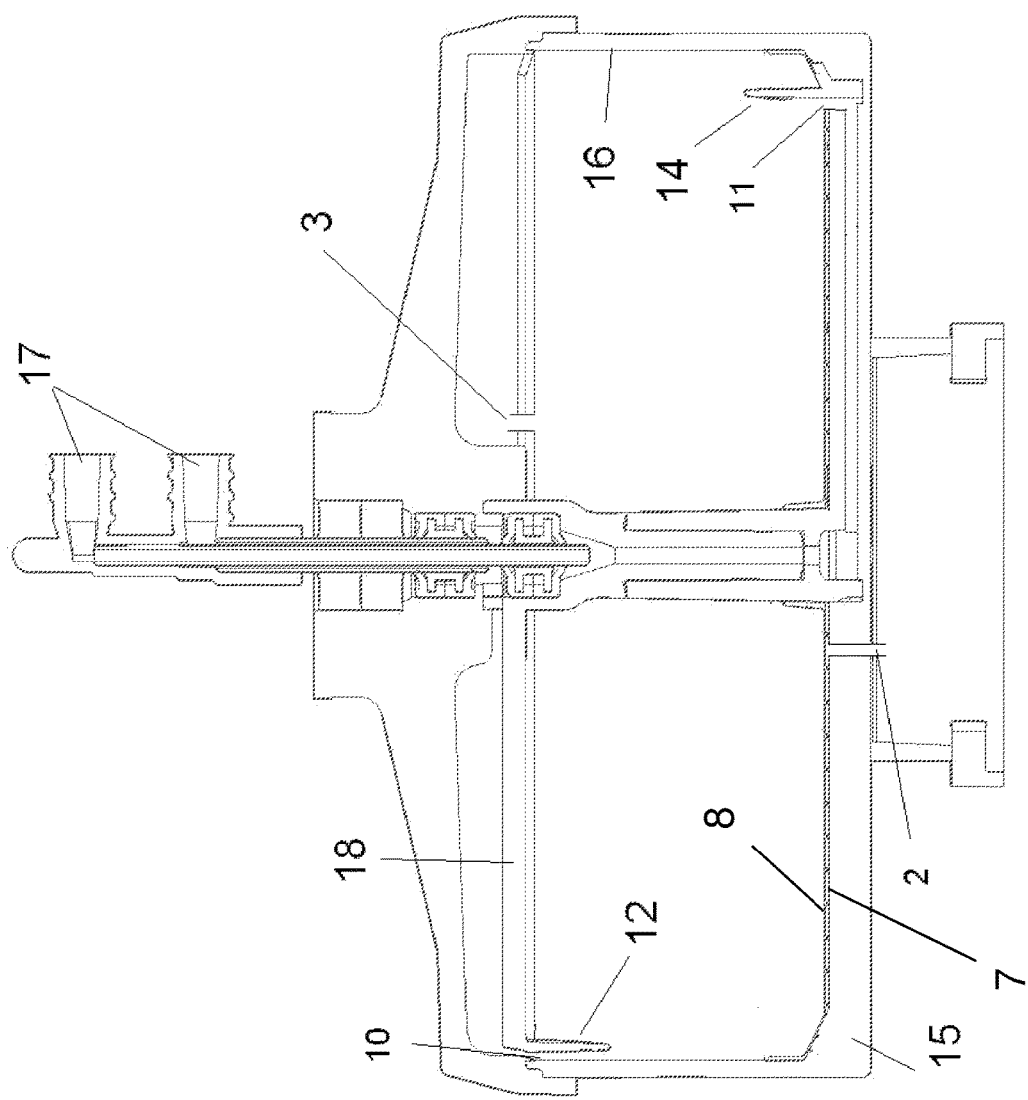
FIG. 2 is a cross sectional view of the centrifugation chamber with at least one layer for cell culturing with a gas permeable membrane.
Figure 3:
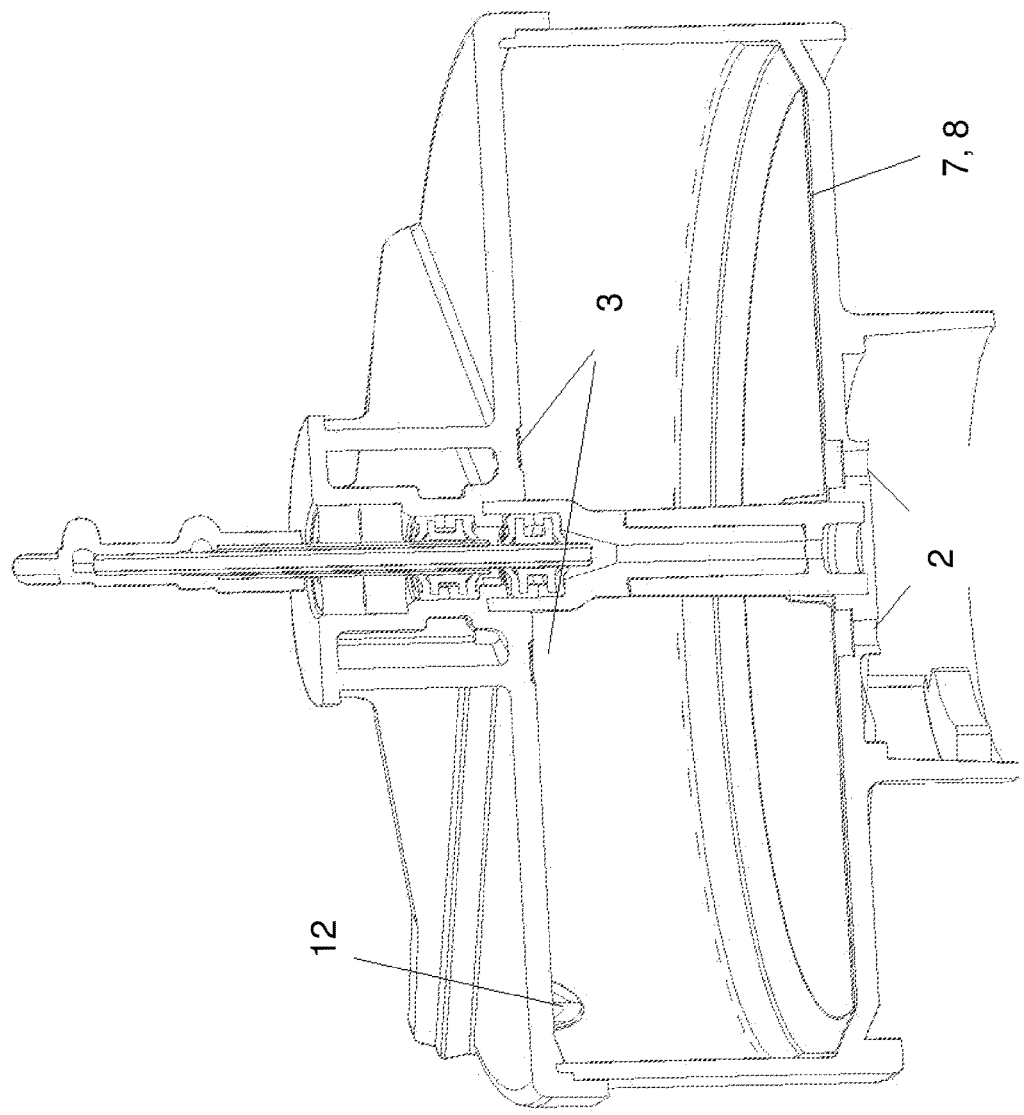
FIG. 3 is a cutaway, perspective view of the centrifugation chamber with at least one layer for cell culturing with the gas permeable membrane.

FIGS. 2 and 3 show by way of example centrifugation chambers according to the invention, using a single layer. These chambers comprise a gas-permeable membrane (8) as the layer for cell culturing which is disposed on a support structure (7) or the base plate (15). Gas necessary to supply the cells are distributed by diffusion through gas-permeable membrane (8) and are homogeneously distributed over the whole area of the membrane. The gases can enter the chamber via at least one port (2) to the volume between the membrane (8) and the support (7). Gas which is not consumed by the cells may exit the chamber via port (3) in the cover plate. Accordingly, in one embodiment, the gas permeable membrane may be disposed on the base plate, so that the base plate may be covered with the gas-permeable membrane, and the gas permeable membrane may be coupled to at least one gas port by the at least one opening.

Figure 6:
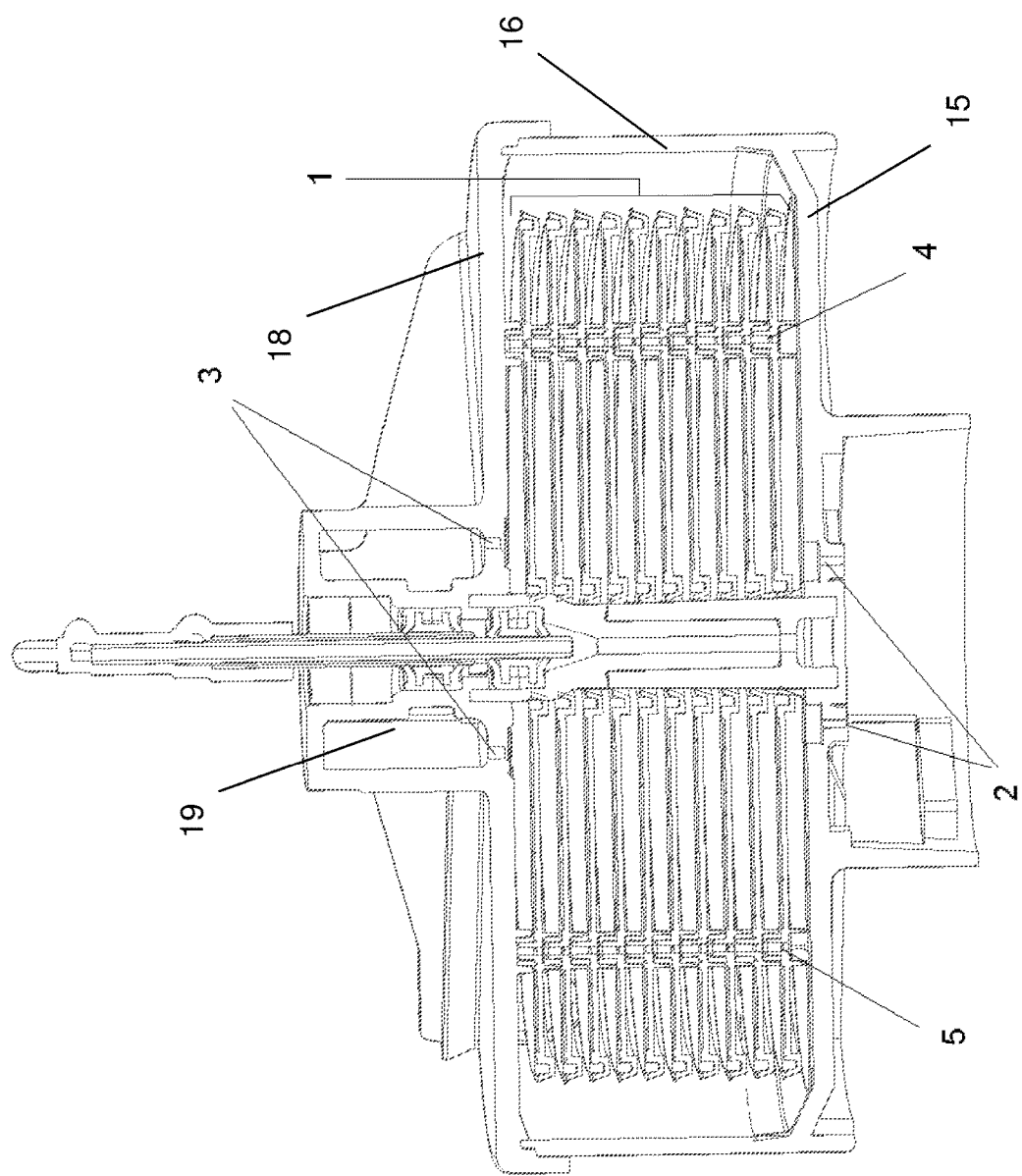
FIG. 6 is a cross sectional view of one embodiment of the centrifugation chamber with a plurality of layers in a stack.

FIG. 6 shows, by way of example, a centrifugation chamber for a plurality of layers arranged in a stack, according to the invention. The chambers may comprise a stack of layers 1 for cell culturing, wherein the layers consist of gas-permeable membranes applied on support structures. The gases may be homogeneously distributed over the whole volume between the membranes and the respective support structure and can supply the cells by diffusion through the gas-permeable membranes. The gases can enter the chamber via at least one port 2 to the volume below the first layer. Gas which is not consumed by the cells may exit the chamber via at least one port 3 in the cover plate. The layers in the stack are interconnected by openings (4) and (5) to allow gas flow through the chamber. Accordingly, each layer for cell culturing may include at least one opening coupled to at least one of an adjacent layer and at least one gas port.

The centrifugation chamber, according to the invention, can be used as or in a cell processing system and/or as a methodology of cell processing. For example, cell processing, according to the invention, can be performed by first expanding a sample of cells by cell culturing. The resulting cell suspension may subsequently be separated into two or more fractions by centrifugation. The separation process may involve one or more washing steps and the desired target cells may be expanded in an additional culturing step.

Another variant of cell processing, according to the invention, may involve enrichment of the desired target of sample cells in a first centrifugation step including one or more washing steps to remove unwanted cells. The thus enriched cell fraction comprises the desired cells which can then be expanded by a subsequent cell culturing step.

The centrifugation chamber may be especially suitable for processing cells originating from blood or bone marrow, like leukapheresis or similar samples.

Gas Permeable Membrane

The gas-permeable membrane, according to the invention, may serve as a layer for cell culturing. Supply of gasses to the cells in the centrifuge chamber, according to the invention may be achieved by gas diffusion through the membrane.

The gas-permeable membrane may be manufactured from polystyrene, silicone like SILPURAN 6000/50 or SILPURAN 2450 (Wacker Chemie AG), polymethylpentene or carbon film and may by glued, welded or press-formed on the support structure or on the base plate of the chamber in a water-tight and gas-tight manner. Accordingly, the gas-permeable membrane may be coupled to at least one of the support structure and the base plate in a gas tight manner.

In order to enhance the homogeneous distribution of the gases to the gas-permeable membranes, each gas-permeable membrane can be provided with a plurality of spacer elements or channels on their gas-side. The spacer elements or channels of the permeable membrane may ensure sufficient volume and/or a defined space between the membrane and the support structure or the membrane and the base plate to enhance the distribution of gases over the surface of the membrane. Accordingly, the support structure may be provided with channels.

Figure 10:
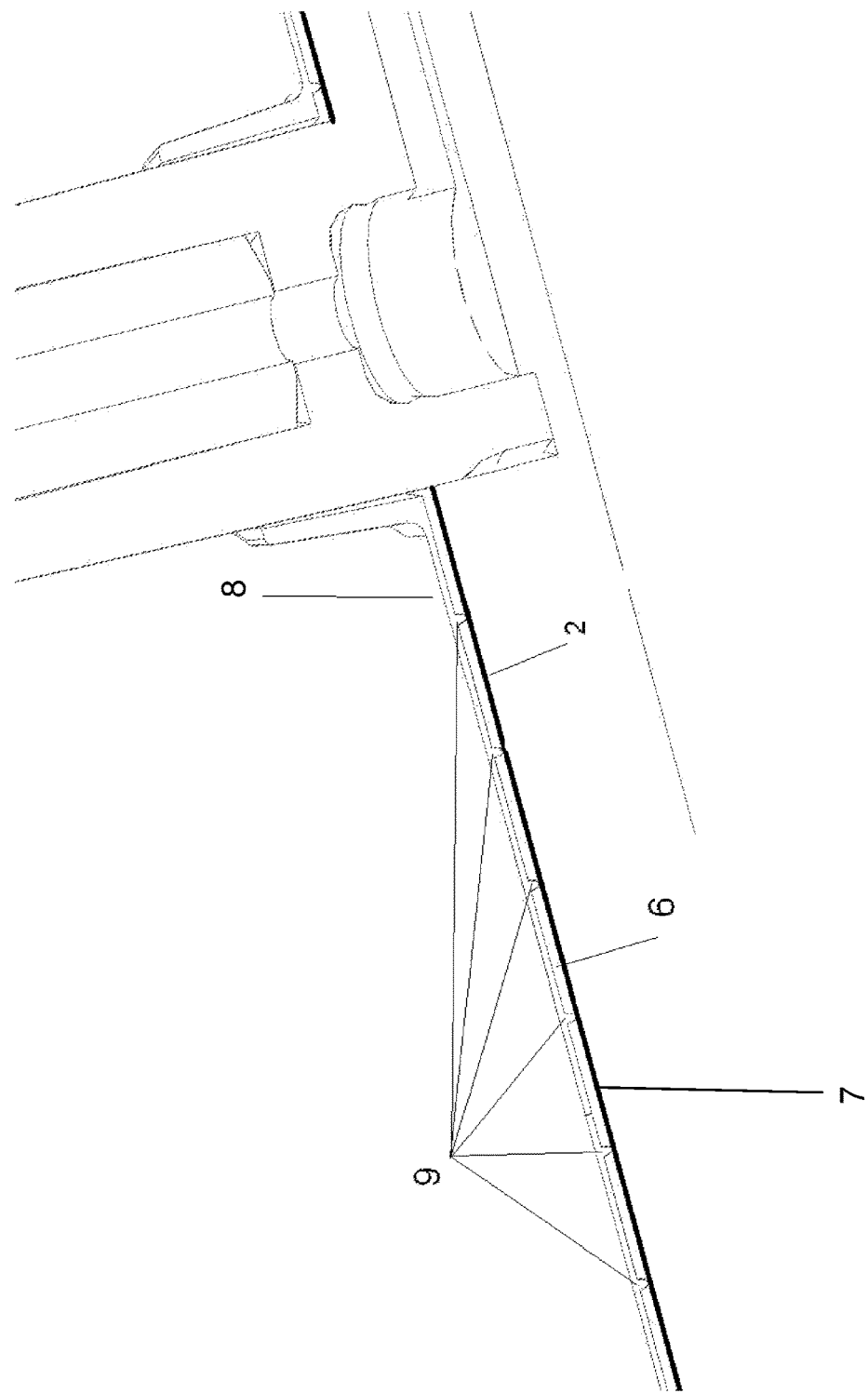
FIG. 10 is a close-up, cutaway, perspective view of the gas-permeable membrane with a plurality of spacer elements which provide a volume between the membrane and the support structure.

Spacer elements may have the form of dots, textures or tappets or the like and have a height of 0.1 to 0.5 mm. The channels can have a depth and width of 0.1 to 0.5 mm and can be arranged in any geometrical form like spiral shaped, maze or labyrinth-like fashion. FIG. 10 shows by way of example a gas-permeable membrane with a plurality of spacer elements 9 to provide a volume 6 between the membrane (8) and the support structure (7). Of course, the channels of spacer elements are oriented between the gas-permeable membrane and the support structure or the base plate and are not in contact with the cells. Accordingly, the gas-permeable membrane, the support structure and the base plate are provided with a plurality of spacer elements.

The gas-permeable membrane (8) may preferably be made with an optically transparent material suitable for optical microscopy, i.e. has a haze and light transmittance comparable to glass. The surface of the gas-permeable membrane should be as smooth as possible for this purpose.

Figure 8:
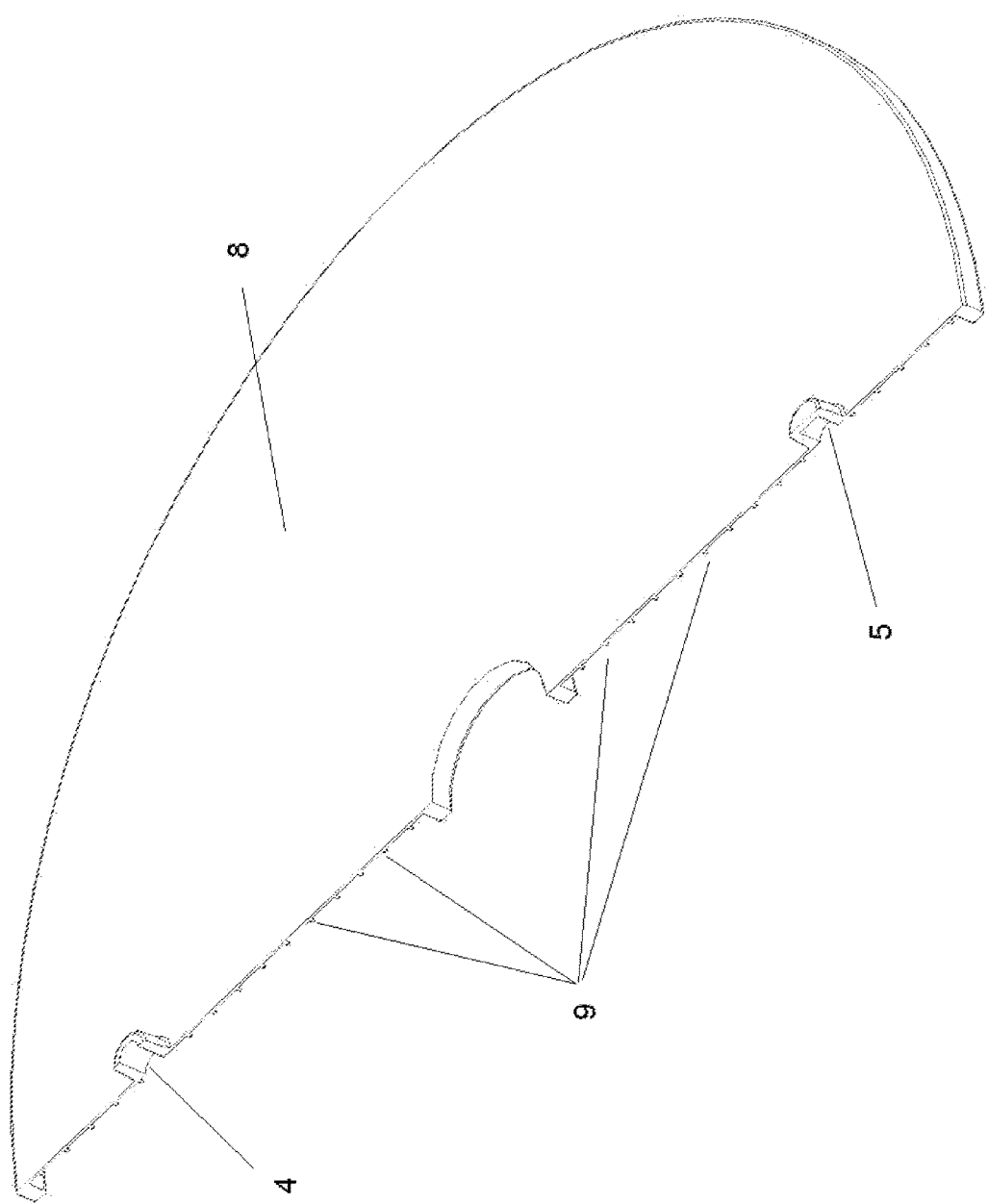
FIG. 8 is a cutaway, perspective view of a single layer of the gas-permeable membrane with openings in the support structure.

Since the layers in the stack are interconnected by openings, the membranes may be provided with openings too. FIG. 8 shows a membrane 8 provided with spacer elements 9 and openings 4, 5 for gas transfer between the layers. The openings may be provided with vents, either as non-return valves or valves which open at a certain gas pressure.

Support Structure

The support structures may give the gas-permeable membranes sufficient mechanical stability under centrifugation conditions and provide a defined volume under the membrane. The first support structure is located on or over the base plate. Alternatively the first support structure, may be used as a support for the first gas-permeable membrane. Accordingly, the gas permeable membrane may be disposed on a support structure.

In order to allow the removal of liquids from the chamber through the openings connected to the port for input and/or output of liquids in the rotational axis, the support structure may be provided with orifices or openings at the appropriate places. If the chamber is provided with deflectors at the openings, the support structure may be either provided with openings or orifices for the deflectors or the deflectors are attached to the support structure.

Figure 14B:
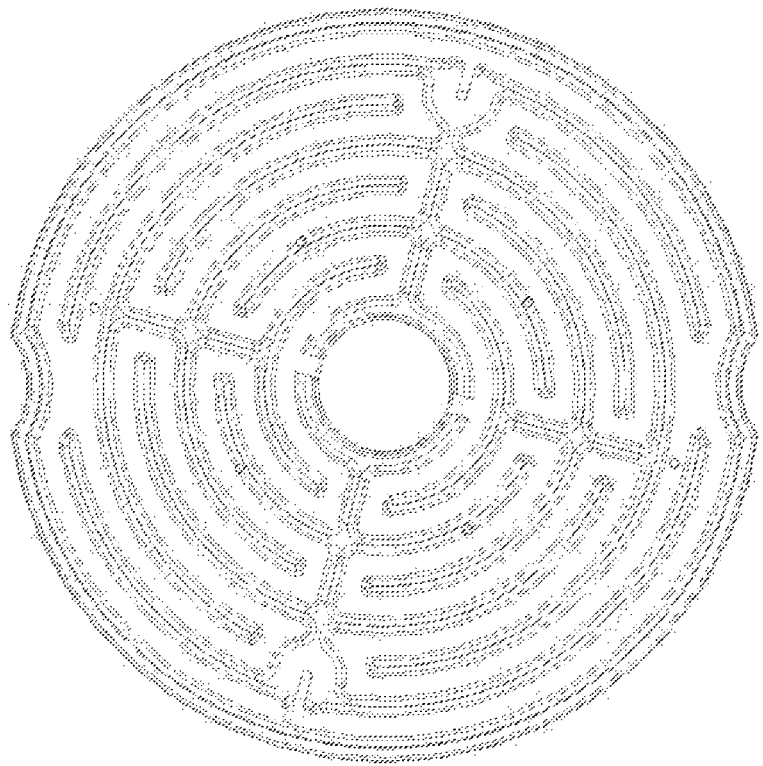
FIGS. 14a and 14b show two embodiments of support structures with channels.
Figure 14A:
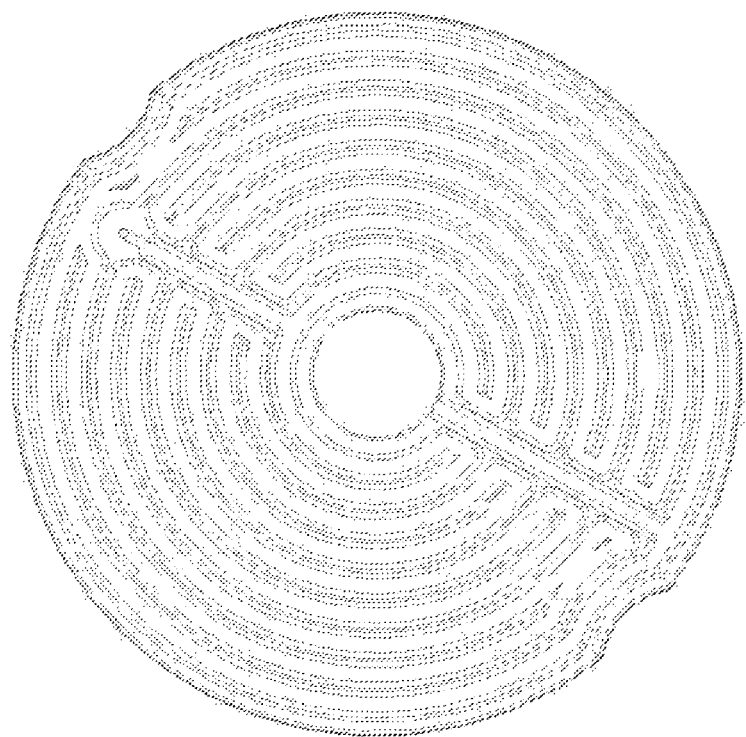

In order to enhance the homogeneous distribution of the gases to the gas-permeable membranes, the support structures can be provided with a plurality of spacer elements or channels. Spacer elements may have the form of dots, textures or tappets or the like and have a height of 0.1 to 0.5 mm. The channels can have a depth and width of 0.1 to 0.5 mm and can be arranged in any geometrical form like spiral shaped, maze or labyrinth-like fashion. FIGS. 14a and 14b show, by way of example, two support structures (7) with channels.

The support structures, and the gas permeable membranes, may preferably have an optical transparency suitable for optical microscopy, i.e. has a haze and light transmittance comparable to glass. The surfaces of the support structure should be as smooth as possible for this purpose.

Figure 9:
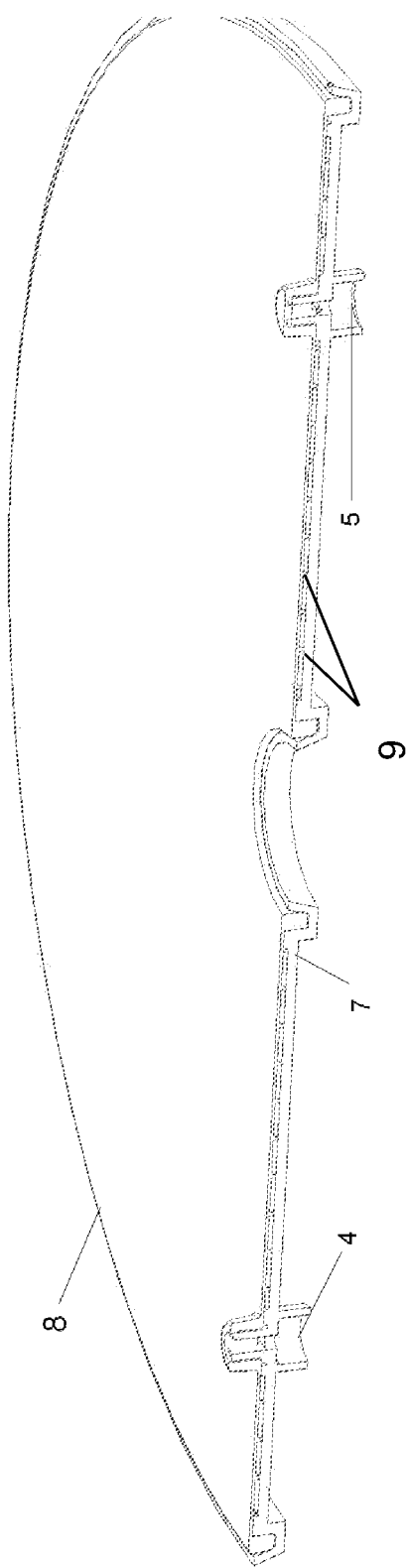
FIG. 9 is a cutaway, perspective view of single layer of a gas-permeable membrane with openings having a neck which fits into or on the neck of the next layer.

Since the layers in the stack are interconnected by openings, the support structures may be provided with openings too. FIG. 9 shows a gas-permeable membrane 8 attached to a support structure 7, each provided with openings 4 and 5 for gas transfer between the layers. The openings may be provided with vents, either as non-return valves or valves which open at a certain gas pressure.

Layer for Cell Culturing

Gas-permeable membrane (8) and the support structure (7) form a layer for cell culturing. This layer can be fixed at the rotational axis of the chamber. Hereby, the layer is subjected to the same rotational speed as the chamber/the rotational axis. In a one variant of this embodiment of the invention, the cells adhere to the membrane and can be cultivated on the layer at low rotational speed of the chamber. At higher speeds of rotation, the cells are removed by the centrifugal forces from the membrane and are suspended in the cell culturing media. The suspended cells can be separated from each other by centrifugation of the chamber according to their respective speed of sedimentation.

In another variant of this embodiment, the layer is not fixed at the rotational axis of the chamber, but can rotate freely about the rotational axis of the chamber. In one variant of the invention, the cell media is distributed through the chamber by rotation of the layer relative to the chamber. The layer will not remain idle, but will rotate in a slow manner similar to the movement of a roller fermenter.

In a yet another variant of this embodiment, the layer is not tightly fixed at the rotational axis of the chamber, but can rotate for about a quarter to half of a turn until further free rotation is blocked. In this variant, the chamber may change its direction of rotation frequently and the cells are supplied by cell media is distributed by the movement of the chamber. At higher speeds of rotation, the free rotation of the layer is blocked and the cells are removed from the surface due to shear forces. After being dispersed in the cell culturing media, the cells can be separated under centrifugal forces according to their respective speed of sedimentation.

Stack of Layers for Cell Culturing

Figure 7:
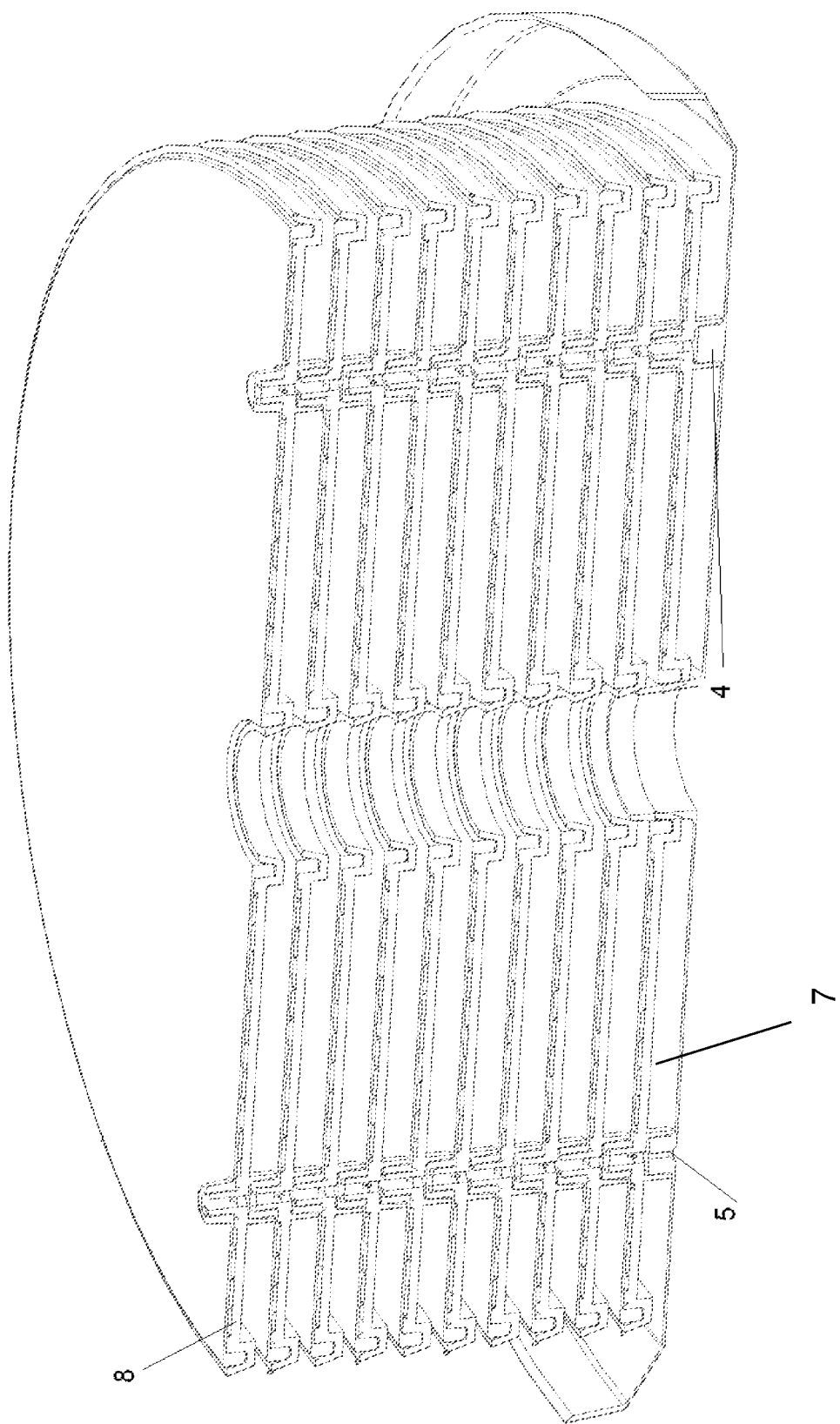
FIG. 7 is a cutaway, perspective view of one embodiment of the stack of layers for cell culturing, each layer consisting of a gas-permeable membrane on a support structure.

The centrifugation chamber, according to the invention, may comprise a stack of layers for cell culturing, each layer consisting of a gas-permeable membrane applied on a support structure. Preferably, the stack may comprise 2 to 20 layers, most preferred between 5 and 10. The layers may have a distance to each other of between 2 and 10 mm, preferably 2 to 5 mm. FIG. 7 shows an example of such a stack of ten, each with gas permeable membranes 8 and support structures 7 with layer interconnecting ports 4 and 5. Accordingly, each layer may be connected to at least one of an adjacent layer and at least one gas port by at least one opening, and the plurality of layers for cell culturing may be disposed on top of one another in a stack. The first layer of the stack may be connected to the at least one gas port.

In order to provide a sufficient flow of gas through the chamber i.e. between the layers, the gas-permeable membranes and the support structures can be provided with openings having a neck which fits into or on the neck of the next layer. For example, the neck of the openings of the support structure may have a larger diameter than the neck of the openings of the adjacent gas-permeable membranes. Such necks can be stacked into each other, thereby providing a gas-tight channel connecting the layers in a stack. FIGS. 8 and 9 show openings 4 and 5 of the support structure and gas-permeable membranes having necks with different diameters.

In other words, the gas-permeable membrane and the rigid support may each have a through hole structure formed therein, wherein the through hole structure in the membrane fits over the through hole structure in the rigid support, thereby defining their relative orientation, and wherein the membrane further has spacers that allow the flow of gas from the through hole structures to a volume between the membrane and the rigid support. The base plate may be coupled to a gas port and to at least one gas permeable membrane, so that the gas port is in gaseous communication with the at least one gas permeable membrane.

In some embodiments, the through hole structure in the rigid support may have a narrower dimension on one side than an obverse side, such that the through hole structure one layer can accept the through hole structure on an adjacent layer in an interlocking, stacked structure. In other embodiments, each layer may have at least two through hole structures on the membrane and rigid support, wherein the at least two through hole structures are about 180 degrees apart on the surface of the membrane or rigid structure.

In other embodiments, one of the two through hole structures is sealed on each layer, defining a serpentine gas path for the gas through the centrifuge chamber. Further, the gas-permeable membrane may have a gas-tight seal at its inner and outer diameter against the rigid support, forming an enclosed volume between the gas-permeable membrane and the rigid support. The support structure may also be provided with channels. These features are shown clearly in FIGS. 8 and 9.

It may be possible to direct the gases in a predefined pathway over the layers or through the stack by providing the openings in the support structure and gas-permeable membranes in an open or closed condition. In another embodiment of the invention, layers (consisting of support structure and gas-permeable membrane) may be provided with two openings having necks, of which one may be closed and the other open. Accordingly, as shown in FIGS. 7, 8 and 9, each layer for cell culturing may comprise at least one opening interconnecting the layers in the stack and wherein the openings of two adjacent layers are located opposite each other and on a line intersecting the rotational axis. Having the support structure so configured with through hole structures, a plurality of layers for cell culturing may be disposed on top of one another in an interlocked stack.

Figure 11:
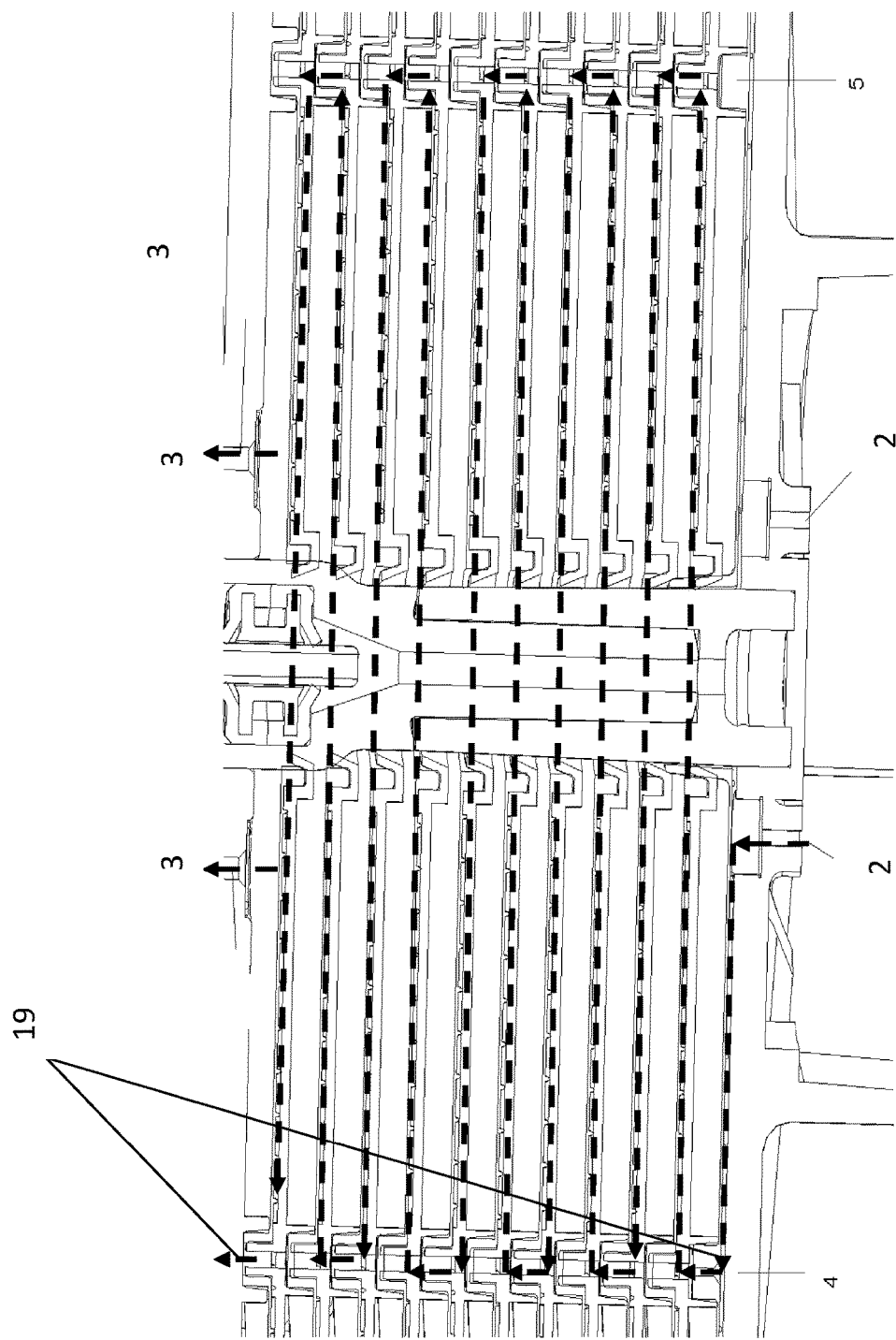
FIG. 11 is a cross sectional cutaway view of a first configuration of the plurality of gas permeable membranes and support structures, showing the gas flow through the assembly.
Figure 13:
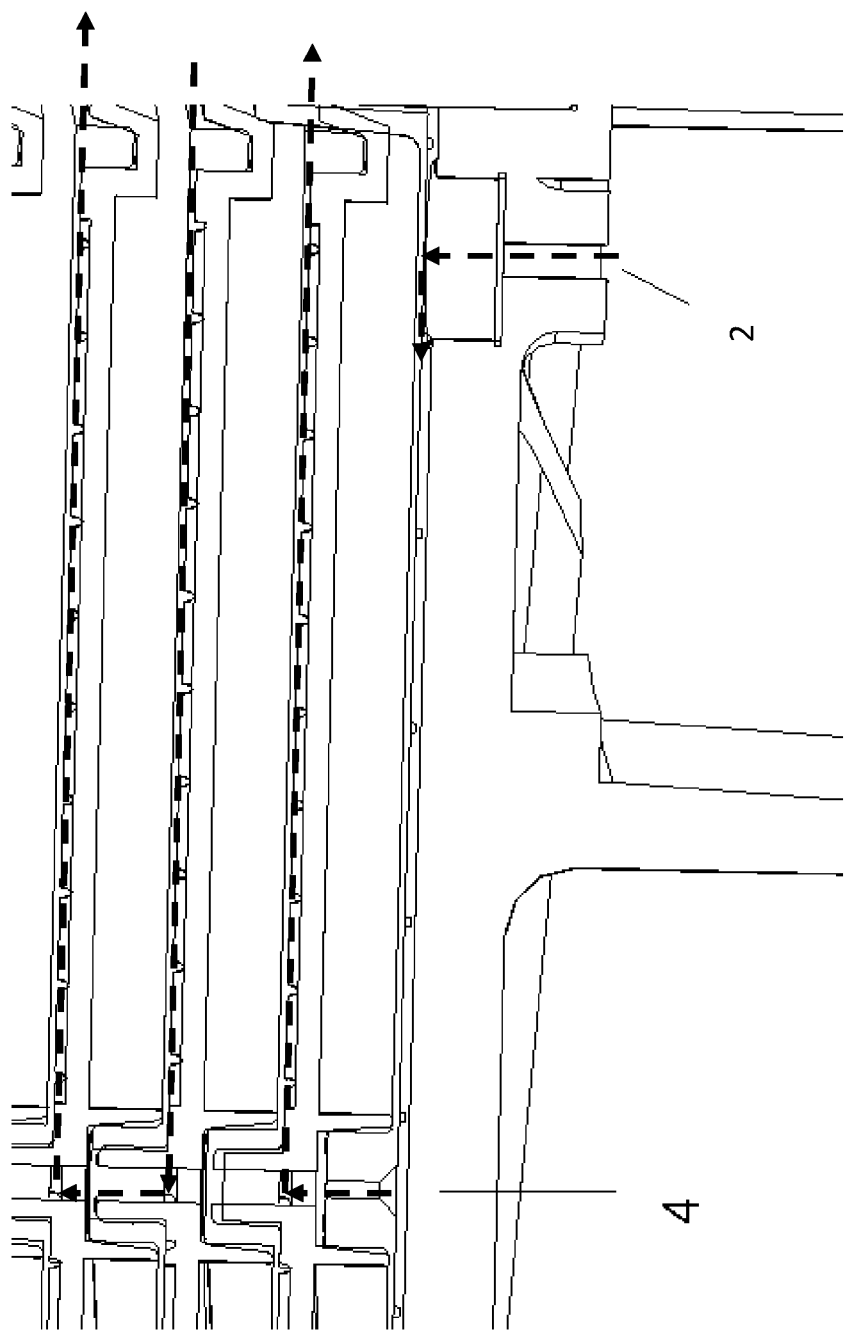
FIG. 13 shows a close-up of the gas passage through the layers.

By stacking together such layers in a way that a closed opening is on top of an open one, gases may be forced so move in a serpentine (i.e. zig-zag or back-and-forth) path through the chamber. FIG. 11 shows this embodiment, where the gases (depicted as dotted line) enter the first layer via orifice 2 and are guided by opening 4 and 5 through all layers until leaving the chamber a by openings 3. FIG. 13 shows a close-up of the gas passage through 4 layers.

Figure 12:
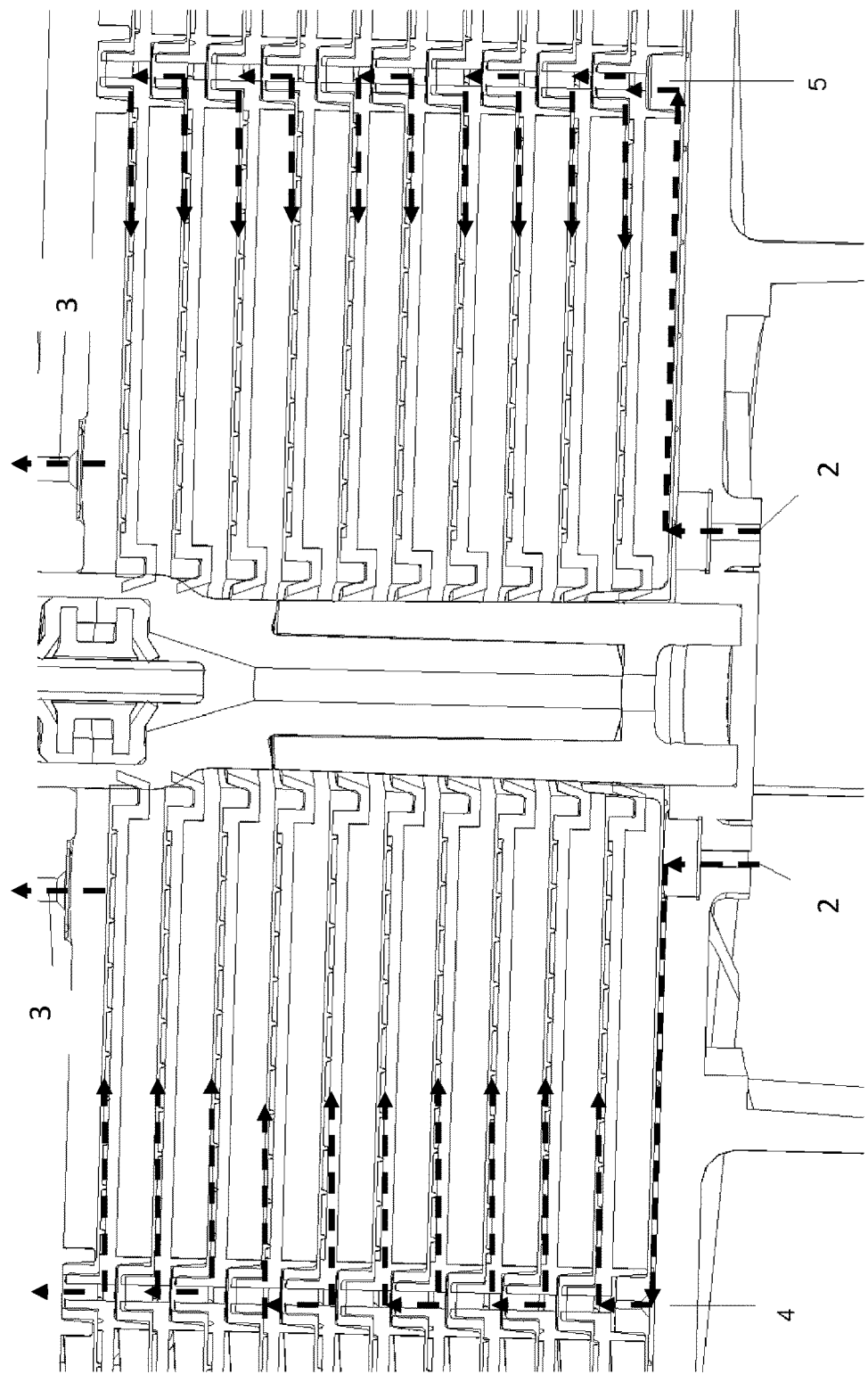
FIG. 12 shows a second configuration of the plurality of gas permeable membranes and gas flow therethrough.

In an alternative embodiment, the layers (consisting of support structure and gas-permeable membrane) may be provided with two openings having necks, of which both are in the open state. FIG. 12 shows this embodiment, where the gases (depicted as dotted line) may enter the first layer via orifices 2 and may be guided through openings 4 and 5. In this embodiment, the chamber can be put under a constant gas pressure by closing openings 3 (or providing openings 3 with appropriate vents) and supplying fresh gas via orifices 2. The gas may be distributed through the chamber/layers according to the consumption of the cells.

The stack of layers for cell culturing can be fixed at the rotational axis of the chamber. Hereby, the stack may be subjected to the same rotational speed as the chamber around the rotational axis. In a first variant of this embodiment of the invention, the cells may adhere to the membrane and can be cultivated on the layers at low rotational speed of the chamber. At higher speeds of rotation, the cells may be removed by the centrifugal forces from the membranes and may be suspended in the cell culturing media. The suspended cells can be separated from each other by centrifugation of the chamber according to their respective speeds of sedimentation.

In another variant of this embodiment, the stack may not be fixed at the rotational axis of the chamber, but may rotate freely about the rotational axis of the chamber. In this variant of the invention, the cell media may be distributed throughout the chambers by rotation of the layers relative to the chamber. The stack may not remain idle, but may rotate in a slow manner similar to the movement of a roller fermenter.

In a yet another variant of this embodiment, the stack may not be tightly fixed at the rotational axis of the chamber, but may rotate for about a quarter to half of a turn until further free rotation is blocked. In this variant, the chamber may change its direction of rotation frequently and the cells and supplied cell media may be distributed by the movement of the chamber. At higher speeds of rotation, the free rotation of the stack may be blocked and the cells may be removed from the surface due to shear forces. After being dispersed in the cell culturing media, the cells may be separated from each other by centrifugation of the chamber according to their respective speed of sedimentation.

Centrifugation Chamber

The chamber may have an inner diameter of 2 cm to 20 cm (preferably 8 to 15 m) and an inner height of 5 mm to 10 cm (preferably 2 cm to 7 cm.) The total volume of the chamber may be between 10 cm$^3$ and 2000 cm$^3$ (preferably between 200 cm$^3$ and 1000 cm$^3$).

The centrifugation chamber of the invention may consist of a chamber made up of a cup like base and a cover plate and was shown for a single layer in FIG. 2, and for a stack of layers in FIG. 6. In either case, the chamber, base and cover plate can be substantially round or circular shapes in order to simplify production and to reduce any imbalance during the centrifugation process. In another embodiment, at least the cylinder may be a slightly elliptical shape, with a diameter in a first dimension being 0.5 mm to 10 cm, (preferably 0.5 mm to 5% larger in a second dimension oriented perpendicular to the first dimension). For example the cylinder may have in a first dimension a diameter of 120 mm and in a second dimension being orientated perpendicular to the first dimension a diameter of 122 mm.

The base and cover may have the same elliptic shape or can be round/circular objects. It is preferred that the tubes comprising openings with deflectors may be oriented in the larger dimension of the elliptical cylinder. In this case, the cells will be moved by the force of centrifugation along the cylinder walls in the direction of the larger dimension of the cylinder i.e. toward the openings.

The chamber and the support structures may be made of various materials such as ceramics, polystyrene (PS), polyethylene (PE), polypropylene (PP), polyvinylchloride, polycarbonate, glass, polyacrylate, polyacrylamide, polymethylmethacrylate (PMMA), and/or polyethylenterephtala (PET). Polytetrafluorethylen (PTFE) and/or thermoplastic polyurethane (TPU), silicone or compositions comprising one or more of the above mentioned materials. Furthermore, the chamber may comprise or be made of biodegradable material such as collagen, chitin, alginate, and/or hyaluronic acid derivatives, polyactide (PLA), polyvinyl alcohol (PVA), olyglycolida (PGA) and their copolymers.

Cell processing according to the invention may involve separation of the cell suspension into two or more fractions by centrifugation. After separating the cell fractions, unwanted liquids or cell suspensions may be removed from the chamber via openings in the base plate and/or cover plate and through the input/output ports. A cell separation step may optionally comprise one or more washing steps wherein washing liquids may be separated from the cell suspension centrifugation and may be subsequently removed via the openings and the input/output ports of liquids of the chamber.

Addition and removal of cell suspension, nutrition liquids and/or washing liquids from/into the centrifugation chamber may be possible via the ports for input/output of liquids which are connected to appropriate openings in the chamber.

The openings of the chamber (for example 10 and 11 in FIG. 2) may be shaped as holes or line entries and their position in the centrifugation chamber may be configured such that they are best suited for the separation of a particular sample or for the draining of particular fluids in or out of the chamber. Depending on the components of a particular sample and the relative volume of each component in the sample, the openings may be positioned in such a way that the fastest removal and/or detection of a particular layer can be achieved. In addition, the size of the openings may be optimized for the desired layer, for example in view of the size of the target cells and/or optimized volume flow.

In case the cylinder is shaped slightly elliptically, it may be preferred that the openings with deflectors are oriented in the larger dimension of the elliptical chamber. In this case, the cells may be moved by the force of centrifugation along the cylinder walls in the direction of the larger dimension of the cylinder i.e. toward the openings.

In a further embodiment, the chamber, according to the invention, may comprise a means for controlling the progress of the sample separation, positioned at the base plate or the cover plate of the chamber. The means for controlling the progress of the sample separation may preferably be positioned at a channel or at a gap located in the base plate or the cover plate of the chamber such that the sample can enter the channel or gap during the centrifugation and thus become detectable. Due to the centrifugal force, different components of the sample may form layers, which are detectable by light, for example with a camera or a light detector. Thereby, a signal may be generated that may allow for determining when the layer formation or sample separation is complete. Suitable means for controlling the progress of the sample separation are disclosed in WO 2009/072006 or WO 2009/072003 incorporated herein by reference.

The centrifugation chamber may be used for cell separation processes, for cell culture purposes and for further processing of the cells grown therein. The chamber may allow a large range of cell culture methods to be performed, such as growing of cells, separating, washing, enriching the cells or differentiating cells, or other types of cell culturing techniques For these purposes, the chamber may comprise further inlet/outlet openings, e.g. for gas, cell culture media or the like. Cell culture conditions are known in the art.

According to the invention, the cell culturing process within the chamber, with or without centrifugation conditions may be performed until the desired number of target cells is achieved or the capacity of the layer is exhausted. The duration of the process may depend on the desired quantity of target cells and is not limited. Typically, the process for cell culturing may take between 1 and 24 hours.

Centrifugation may preferentially be carried out between 10 and 2000×g, preferably between 100 and 500×g. In a preferred embodiment, the chamber may be heated and cooled to provide for a temperature appropriate for the sample to be centrifuged. For this purpose, a heating and/or cooling means may be located at the chamber or surrounding the chamber.

Chamber With Deflectors for Enhanced Separation Process

Overall, cell processing may be enhanced or accelerated by modifications of the chamber, especially by providing the openings of the input/output ports of liquids into the chamber with deflectors.

In another embodiment of the centrifuge chamber according to the invention, at least one port for input and/or output of liquids may be connected to openings located in the base plate and/or cover plate into the centrifuge chamber and at least one opening may be provided with at least one deflector having a width at its base of at most $\frac{1}{10}$ of the inner circumference of the cylinder. Accordingly, the at least one liquid port may be connected to an opening in at least one of the base plate and cover plate and the opening is provided with at least one deflector. The at least one deflector may have a width at its base of at most $\frac{1}{10}$ of the inner circumference of the chamber In a first embodiment of the invention, at least one deflector may be located between at least one opening and the cylinder or outer wall. Located here, this deflector may shield the opening from the volume between opening and cylinder and may prevent, during draining of this volume, the unwanted sucking of liquid from another part of the chamber i.e. from the volume between the opening and the cylinder of the chamber. This embodiment may be shown by way of example in FIG. 2 (omitting the stack of layers) with opening 11 and deflector 14. In this embodiment, the chamber may be provided with two, four, six or eight openings in both the base and cover plate.

In a second embodiment, at least one deflector may be located between at least one opening and the rotational axis of the cylinder. Different from the first embodiment, this deflector may shield the opening from the volume of the chamber between opening and cylinder wall and prevents sucking liquid from this volume when draining the internal volume of the chamber. An example of this embodiment may be shown, in FIG. 2 (omitting the stack of layers) with opening 10 and deflector 12. In this embodiment, the chamber may be provided with two, four, six or eight openings in both the base and cover plate.

In a third embodiment of the invention the chamber may include deflectors in both locations of the first and second embodiment, i.e. at least one deflector is located between at least one opening and the cylinder and at least one deflector is located between one opening of a second tube and the rotational axis of the cylinder. The location of the deflectors with respect to the openings and/or the distance to the cylinder may be the same or different. FIG. 2 (omitting the stack of layers) shows this embodiment of the invention with opening 10, 11 and deflector 12, 14. In this embodiment, the chamber may be provided with two, four, six or eight openings in both the base and cover plate. Accordingly, at least one deflector may be substantially parallel with the outer wall of the chamber and may have a width of 5 to 50 times the width of the opening at which it is located. The first deflector may be located between at least one opening and the rotational axis of the cylinder and a second deflector may be located between at least one opening and the outer wall of the chamber.

In the third embodiment of the invention, the two openings of the chamber may be connected or give access to two different volumes of the chamber and may be used to drain the liquid provided therein.

With the shielding effect of the deflectors, according to the invention, re-mixing of the layers during draining may be reduced, resulting in higher purity of the fractions obtained when draining the layers and/or the enablement of higher draining speed.

The deflectors utilized in the present invention may preferably be substantially parallel with the cylinder i.e. they are shaped according to the curve radius of the cylinder. The shape of the deflector can be rectangular, triangular, half-round or elliptical. In a preferred embodiment, the deflector may have a broad base located at the opening of a tube and a smaller peak area in order to lower shear forces applied to the cells during centrifugation. The edges of the deflector should be chamfered to avoid cell losses by cutting or ripping of the cellular membrane at the edges. Most preferred, the deflector may be half-round or half-elliptical.

The size of the deflectors should be sufficient to reduce the unwanted volume flow, for example by draining liquid from the volume of the chamber located behind the opening in the direction of the outside of the chamber when the draining of the part of the chamber located towards the rotational axis is desired.

The size of the deflectors may depend on the volume of the chamber, the volume to be shielded and the intended draining speed. For example, the larger the volume to be shielded, the larger the deflector should be. Regardless of its shape, the deflector should have a width at the base (at the opening of a tube) of $1/10$ to $1/60$, (preferably of $1/25$ to $1/40$) of the inner circumference of the cylinder. For example, a cylinder having an inner diameter of 10 cm may be provided with deflectors having a width at the base (at the opening of a tube) of 1 to 2 cm.

The height of the deflector is preferably the same (100%) or smaller, for example, 50 to 95% of the width at the base.

The size of the surface of a deflector may be calculated or estimated from the given ranges in width and height, but is usually between 0.1 cm$^2$ and 10 cm$^2$. In any case, the size of the deflector should not hamper the separation of the sample into layers but to reduce unwanted flow of liquid from the separated layers.

The chamber of the invention may comprise several deflectors, which may have the same or different size and/or height and/or width.

Figure 4:
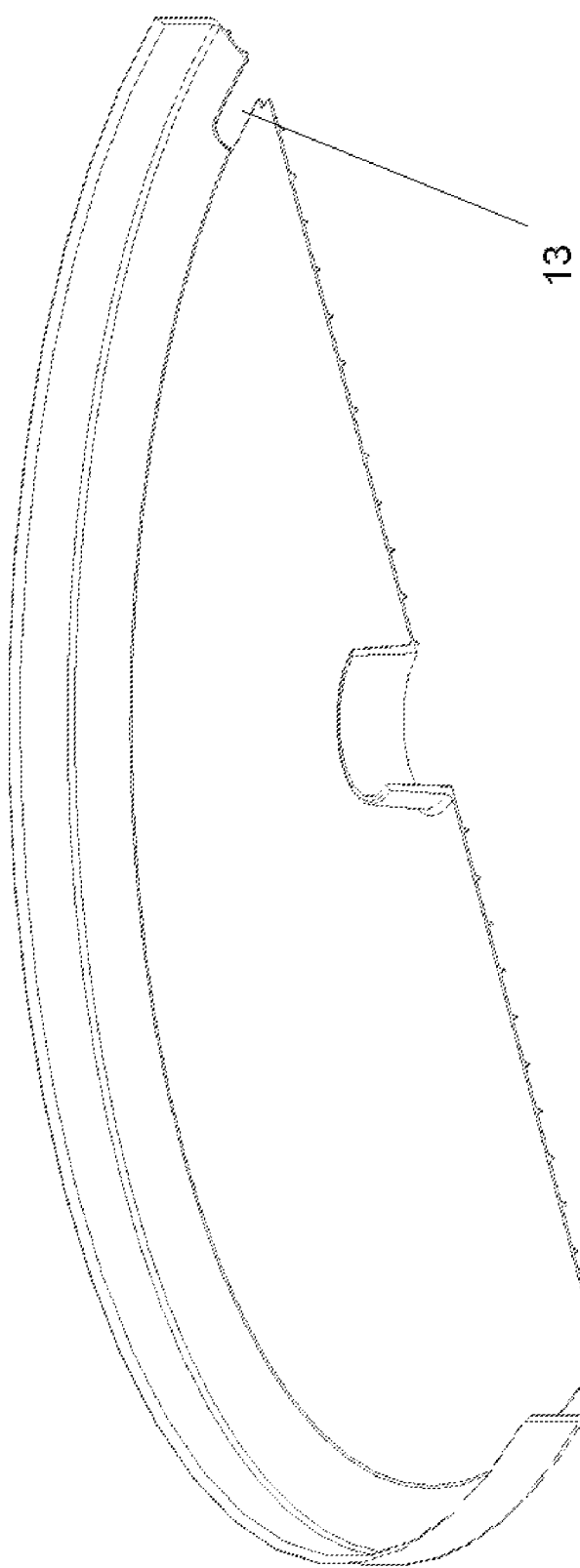
FIG. 4 is a cutaway, perspective view of the layer with a gas-permeable membrane and with openings for deflectors.
Figure 5:
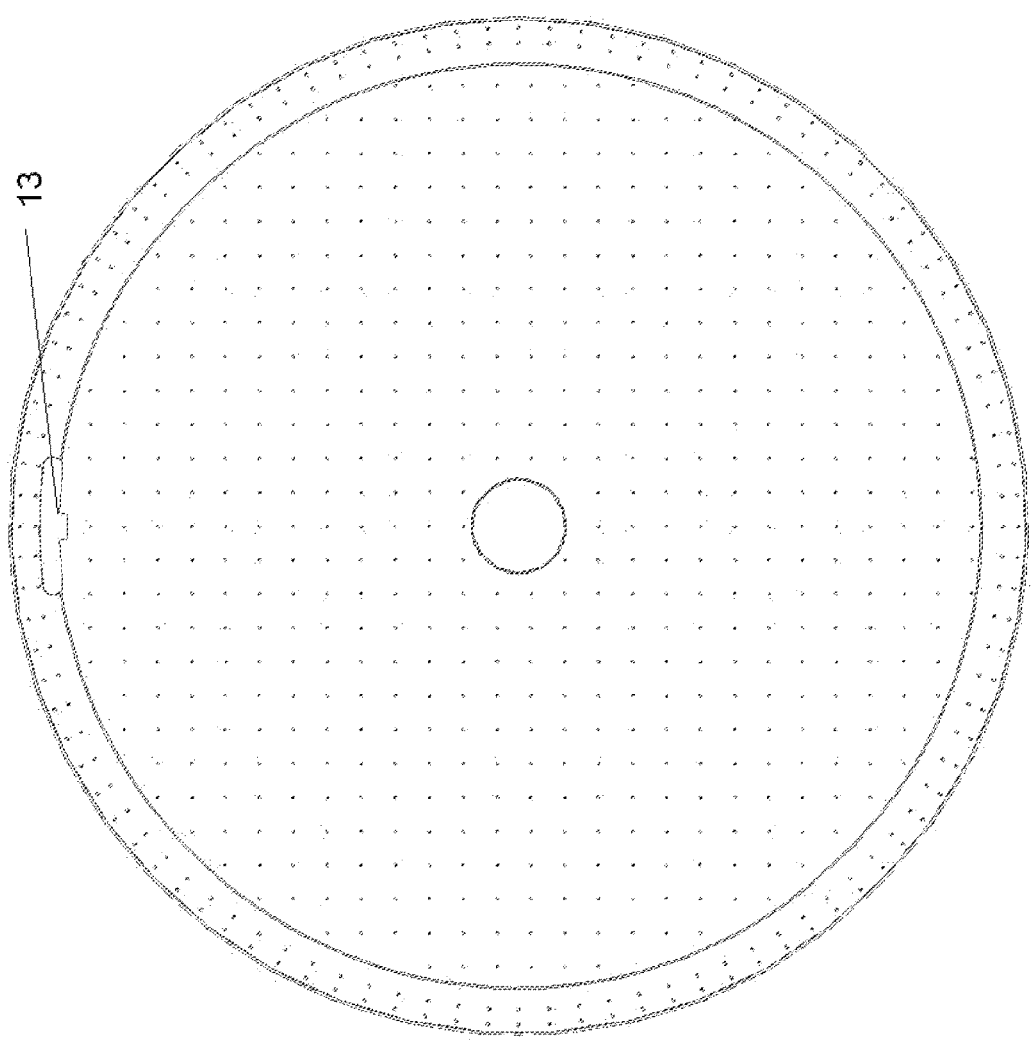
FIG. 5 is a plan view of a gas-permeable membrane with openings for deflectors.

If the chamber of the invention is provided with deflectors at the openings, the gas-permeable membrane and the support structure are provided with orifices or openings for the deflectors and the openings. Gas permeable membranes with openings for deflectors were shown (13) in FIGS. 4 and 5.

A centrifugation chamber, according to the invention, may preferably comprise as shown in FIGS. 2 (omitting the stack of layers) and 6, a rotational axis with a rotating seal and preferably with two fluid lines or input/output ports for liquids 17. The centrifuge chamber comprises furthermore a cover plate 18, a base plate 15 joined by cylinder 16. The base plate 15 is provided with tubes, which are connected to the respective input/output ports 17 and openings 10,11 into the chamber. The openings 10, 11 are provided with deflectors 12, 14.

In the embodiment shown in FIGS. 2 (omitting the stack of layers) and 6, the base plate 15 and the cover plate 18 of the chamber 16 may be provided with at least one each orifice for input 2 and/or output 3 of gases.

The orifices for input (2) and output (3) of gases may be provided with a sterile filter across the direction of gas flow. The chamber may comprise one, two or four orifices for input and/or output of gases. Alternatively, a first and last layer of the stack may comprise openings covered with sterile filters 19 across a direction of gas flow, as shown in FIG. 11.

According to the invention, if the centrifuge chamber is provided with deflector shields, the layers for cell culturing may preferably have a diameter at least 5% smaller than the outer wall diameter of the chamber. For example, the diameter of the layers should preferably be 85 to 95% of the outer wall diameter (16) of the chamber.

Gas-Permeable Membrane with Functionalized Surfaces

In another embodiment of the invention, the gas-permeable membrane may be provided with a functionalized surface i.e. mat be treated with chemical or physical means or may comprise a coating of chemical or physical immobilized bioactive compounds. Accordingly, a surface of the gas-permeable membrane may be functionalized for cell culturing.

The term "functionalized surface of the gas-permeable membrane" as used in this application may include all types of surfaces which can provide a stimulus to a cell. Typically, functionalized surfaces comprise a coating of chemically or physically immobilized bioactive compounds, such as the following:

proteins, peptides, nucleic acids;
spacer molecules enhancing the adhesion of cells or bioactive compounds to the cell modifying surfaces like hydrophilic polymers (functionalized poly lactate, polyvinyl alcohols, polysaccharides; functionalized dextranes);
organic or inorganic particles as carrier of bioactive compounds, especially magnetic particles coated with functionalized poly lactate, polyvinyl alcohols or functionalized dextranes;
substances enhancing cell adhesion, for example polypeptides, lipids, polysaccharides;
viruses and retroviruses or particles thereof
cells which can be used for modification of a target cell, such as antigen presenting cells, "accessory cells" producing certain bioactive factors or cell lines transfected with certain functional molecules.
stimulus provided by mitogens, cytokines, stimulatory antibodies or receptor ligands
stimulus provided by hydrophilic properties of the surface In a variant of the invention, the gas-permeable membrane may be functionalized with any substance which is suitable for cell culture and useful or required to introduce preferable cell culture conditions for a given cell type.

The gas-permeable membrane may be functionalized by a chemical treatment for example with strong bases, oxygen or a mixture of fluorine and oxygen or by a physical treatment with corona or plasma to enhance hydrophilic properties.

The gas-permeable membrane may be functionalized in order to enhance adherence and/or proliferation of cells on the cell modifying surfaces. Suitable substances for functionalization of the gas-permeable membrane are glycoproteins, polypeptides, glycosaminoglycans, disccharides, biotin binding molecules or protein tags. For example, the gas-permeable membrane may be coated with extracellular matrix proteins including all collagen types (I to VIII).

Furthermore, the gas-permeable membrane may be functionalized with an affinity binding system. One of the most widely used affinity binding system is the avidin-biotin or streptavidin-biotin system. For example, the cell modifying surface may be first coated with avidin and/or streptavidin (or derivates thereof) to facilitate binding of a biotinylated molecule like a biotinylated antibody. It may furthermore be possible to coat the cell modifying surface first with biotin (or derivates thereof) to facilitate binding of another molecule functionalized with streptavidin and/or avidin. Both variants may result in high affinity binding of the second molecule to the cell modifying surfaces. The strong interaction between streptavidin or avidin-biotin is made much weaker by using a combination of modified streptavidin or avidin and modified biotin like desthiobiotin or a derivative thereof like DSB-X Biotin (Hirsch et al. 2002: "Easily reversible desthiobiotin binding to streptavidin, avidin, and other biotin-binding proteins: uses for protein labeling, detection, and isolation". Analytical Biochemistry 308: 343-357; US2008/0255004A1). A protein, such as an antibody may be biotinylated with the modified biotin. When this protein is immobilized by binding the modified biotin to an optionally modified streptavidin or avidin molecule bound to the cell modifying surface, it may be released under mild conditions by adding free biotin.

Further affinity binding systems suitable for the cell modifying surfaces may comprise antibodies, for example antibodies against biotin or protein tags for example IIsopeptago, BCCP or Myc-tag.

The gas-permeable membrane may further be coated with libraries of substances synthesized with methods of combinatorial chemistry in order to identify substances which work best as binding system for a given cell type.

Certain bioactive polymers may be used as spacer molecules enhancing the adhesion of cells or the binding of other substances on the gas-permeable membrane like functionalized poly lactic acid, polyvinyl alcohols, polysaccharides or dextranes or derivates thereof. This binding system may be especially useful as basic coating of a gas-permeable membrane produced from a hydrophobic plastic material like poly carbonate, polystyrene or polyethylene. The gas-permeable membrane of the membranes may be coated with highly reactive polymers as e.g. disclosed in U.S. Pat. No. 6,977,138B2.

The gas-permeable membrane may comprise one or more substances which enhance adhesion and/or proliferation of cells. Especially useful may be one or more substances selected from the group consisting of collagen types (I to VIII), fibronectin, gelatin, laminin, elastin, hyaluronic acid, keratan sulfate, chondroitin sulfate, heparan sulfate proteoglycans, poly-d-lysine, avidin, streptavidin, biotin, antibodies, antibodies against biotin or protein tags, protein tags like IIsopeptag, BCCP, Myc-tag, Calmodulin-tag, FLAG-tag, HA-tag, His-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty tag, certia, poly lactate, polyvinyl alcohols, polysaccharides and dextran.

In another variant of the invention, cell modification may comprise cellular modification like activation, proliferation, dedifferentiation and/or differentiation of cells. Accordingly, the cell modifying surfaces of the gas-permeable membrane may be functionalized with any substance which is suitable for cellular modification of cells like cell activation, proliferation, dedifferentiation and differentiation of cells. The gas-permeable membrane may further be functionalized with particles being functionalized with at least one substance suitable for cellular modification of cells like cell activation, proliferation, dedifferentiation and differentiation of cells.

Particular, cell modification by the method and the device of the invention may comprise the alteration of gene expression, protein expression, post-translational or posttranscriptional modifications of genes, mRNAs or proteins, protein phosphorylation, histone modification, or modification of intracellular signaling cascades (e.g. Ca2+ influx).

Furthermore, cellular modification may comprise cell activation for example by agonistic or antagonistic antibodies, cytokines, growth factors, (de-)activating ligands, pharmacologically active substances, mitogens, DNA or RNA-modifying substances.

Cell Processing System

In a further embodiment, the centrifuge of the present invention may be part of a sample processing system, such as known from WO 2009/072006, WO 2009/072003 or EP 0 869 838 B1, which is hereby incorporated by reference. The sample processing unit may be coupled to the input/output port of the centrifugation chamber and may comprise a separation column holder, a pump, a plurality of containers for (intermediate) storage of liquids during the separation process and a plurality of valves configured to at least partially control fluid flow through a fluid circuit and a separation column positioned in the holder.

Cell Culturing With the Centrifugation Chamber of the Invention

Cell culturing may require supply with cell culturing media and gases. Cell culturing media may be either supplied in a constant or batch-wise flow via the i/o ports of the chamber or the chamber is filled once with cell media sufficient for the cell culturing process envisaged. Suitable cell media are known to the person skilled in the art and may include one or more of the following media DMEM, HBSS, DPBS, RPMI, Iscove's medium, X-VIVO™, each optionally supplemented, for example, with fetal calf serum, human serum or serum substitutes or other nutrients or cell stimuli like Cytokines. The media may be standard cell media like the above mentioned media or special media, for example, primary human cell culture (e.g. for endothelia cells, hepatocytes or keratinocytes) or stem cells (e.g. dendritic cell maturation, hematopoietic expansion, keratonocytes, mesenchymal stem cells or T cell expansion). The media may have supplements or reagents well known in the art, for example, albumins and transport proteins, amino acids and vitamins, antibiotics, attachments factors, growth factors and cytokines, hormones or solubilising agents. Various media are commercially available, for example from LifeTechnologies or Sigma-Aldrich.

Temperature and gas composition of the centrifugation chamber may be controlled and adjusted if appropriate for the cell types or the modification steps to be performed. For this purpose, a heating and/or cooling means can be attached to the device of the invention. In the method of the invention, the cells to be cultured may be supplied with gases such as air, $O_2$, $N_2$ and $CO_2$ by diffusion through the gas-permeable membrane.

Use of the Chamber

The chamber according to the invention may, for example, be used in the following processes:

- Cell processing like cell activation, cell proliferation, cell transfection, cell staining followed or subsequent to a separation or washing step
- isolating leucocytes by separating and discharging erythrocytes and plasma from human blood
- isolating certain subpopulations of leucocytes, for example, leucocytes having one or more of the following surface marker CD4, CD8, CD25, CD 34 and/or CD 133 by separating leucocytes from human blood with subsequent cell labelling
- preparation of leucocytes by discharging erythrocytes and plasma from human blood followed by one or more washing steps with cell media and/or density gradient additives
- isolating, enriching or depleting cells having one or more of the following surface marker CD4, CD8, CD25, CD 34 and/or CD 133 from human blood for use in regenerative medicine, peripheral artery, liver disease or cardiac stem cell therapy While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A centrifuge chamber having a rotational axis, an inner circumference and an outer wall, comprising:
   a base plate;
   a cover plate;
   at least one liquid port for liquids;
   at least one gas port for gases; and
   at least one layer for cell culturing, wherein each layer for cell culturing comprises a gas-permeable membrane on which cells are cultured, and a rigid support that supports the gas-permeable membrane, and wherein the both the gas-permeable membrane and the rigid support each have a through hole structure formed therein, wherein the through hole structure in the membrane fits over the through hole structure in the rigid support, thereby defining their relative orientation, and wherein the membrane further has spacers that allow the flow of gas from the through hole structures to a volume between the membrane and the rigid support, and wherein the base plate is coupled to a gas port and to at least one gas permeable membrane, so that the gas port is in gaseous communication with the at least one gas permeable membrane, wherein each layer has at least two through hole structures on the membrane and rigid support, wherein the at least two through hole structures are about 180 degrees apart on the surface of the membrane or rigid structure, and wherein one of the two through hole structures is sealed on each layer, defining a serpentine gas path for the gas through the centrifuge chamber.

2. The centrifuge chamber of claim 1, wherein the through hole structure in the rigid support has a narrower dimension on one side than an obverse side, such that the through hole structure one layer can accept the through hole structure on an adjacent layer in an interlocking, stacked structure.

3. The centrifuge chamber according to claim 1, wherein the support structure is provided with channels.

4. The centrifuge chamber of claim 1, wherein the gas-permeable membrane has a gas-tight seal at its inner and outer diameter against the rigid support, forming an enclosed volume between the gas-permeable membrane and the rigid support.

5. The centrifuge chamber according to claim 1, wherein the gas-permeable membrane is coupled to the rigid layer and the base plate in a gas tight manner.

6. The centrifuge chamber according to claim 1, wherein the gas-permeable membrane and the support structure have an optical transparency suitable for optical microscopy.

7. The centrifuge chamber according to claim 1, wherein a surface of the gas-permeable membrane is functionalized for cell culturing.

8. The centrifuge chamber according to claim 1, wherein the at least one layer for cell culturing has a diameter at least 5% smaller than a diameter of the outer wall of the chamber.

9. The centrifuge chamber according to claim 1, wherein the at least one liquid port is connected to an opening in at least one of the base plate and cover plate and the opening is provided with at least one deflector.

10. The centrifuge chamber according to claim 9, wherein the at least one deflector has a width at its base of at most 1/10 of the inner circumference of the chamber.

11. The centrifuge chamber according to claim 9, wherein the at least one deflector is substantially parallel with the outer wall of the chamber and has a width of 5 to 50 times the width of the opening at which it is located.

12. The centrifuge chamber according to claim 11, wherein a first deflector is located between at least one opening and the rotational axis of the cylinder and a second deflector is located between at least one opening and the outer wall of the chamber.

13. A centrifuge chamber having a rotational axis, an inner circumference and an outer wall, comprising:
    a base plate;
    a cover plate;
    at least one liquid port for liquids;
    at least one gas port for gases; and
    at least one layer for cell culturing, wherein each layer for cell culturing comprises a gas-permeable membrane on which cells are cultured, and a rigid support that supports the gas-permeable membrane, and wherein the both the gas-permeable membrane and the rigid support each have a through hole structure formed therein, wherein the through hole structure in the membrane fits over the through hole structure in the rigid support, thereby defining their relative orientation, and wherein the membrane further has spacers that allow the flow of gas from the through hole structures to a volume between the membrane and the rigid support, and wherein the base plate is coupled to a gas port and to at least one gas permeable membrane, so that the gas port is in gaseous communication with the at least one gas permeable membrane, wherein a plurality of layers for cell culturing is disposed on top of one another in an interlocked stack, and wherein each layer for cell culturing comprises at least one opening interconnecting the layers in the stack and wherein the openings of two adjacent layers are located opposite each other and on a line intersecting the rotational axis, and wherein gas circulates through the stack in a serpentine fashion.

14. The centrifuge chamber of claim 13, wherein a first and last layer of the stack comprise openings covered with sterile filters across a direction of gas flow.

15. The centrifuge chamber according to claim 13, wherein a first layer of the stack is connected to at least one gas port.

\* \* \* \* \*